(12) United States Patent
Seo et al.

(10) Patent No.: US 6,989,456 B2
(45) Date of Patent: *Jan. 24, 2006

(54) PROCESS FOR PRODUCING EDIBLE STEROL FATTY ACID ESTERS

(75) Inventors: Naoko Seo, Fukuyama (JP); Shoji Kaneko, Fukuyama (JP); Fumi Sato, Fukuyama (JP); Seiji Norinobu, Shinagawa-ku (JP); Mitsumasa Mankura, Fukuyama (JP)

(73) Assignee: Ikeda Food Research Co., Ltd., Hiroshima (JP)

( * ) Notice: Subject to any disclaimer, the term of this patent is extended or adjusted under 35 U.S.C. 154(b) by 288 days.

This patent is subject to a terminal disclaimer.

(21) Appl. No.: 10/381,174

(22) PCT Filed: Sep. 26, 2001

(86) PCT No.: PCT/JP01/08378

§ 371 (c)(1),
(2), (4) Date: Mar. 20, 2003

(87) PCT Pub. No.: WO02/27013

PCT Pub. Date: Apr. 4, 2002

(65) Prior Publication Data

US 2005/0100994 A1  May 12, 2005

(30) Foreign Application Priority Data

Sep. 27, 2000 (JP) ............................... 2000-294772
Feb. 5, 2001 (JP) ............................... 2001-028839

(51) Int. Cl.
*C07J 9/00* (2006.01)

(52) U.S. Cl. ...................................... 552/544; 552/547

(58) Field of Classification Search ................ 552/544, 552/547

See application file for complete search history.

(56) References Cited

U.S. PATENT DOCUMENTS 6,660,491 B2 * 12/2003 Norinobu et al. ............. 435/19

FOREIGN PATENT DOCUMENTS

| EP | 0195311 | * 9/1986 |
| GB | 1284814 | 7/1970 |
| JP | 57-063092 | 9/1980 |
| JP | 60-081200 | 10/1983 |
| JP | 61-204197 | 3/1985 |
| JP | 62-048391 | 8/1985 |
| JP | 62-166895 | 1/1986 |
| JP | 61-204197 A . | 10/1986 |
| JP | 61-205212 A . | 11/1986 |
| JP | 62-48391 A | 3/1987 |
| JP | 01-218593 | 2/1988 |
| JP | 04-013608 | 4/1990 |
| JP | 07-007827 | 6/1993 |
| WO | 98 19 556 | 5/1998 |

OTHER PUBLICATIONS

E.C. Needs et al. "Influence of Processing Temperature and Seasonal Change in Diet on Lipase activity a Lipolysis During the Mechanical Separation of Bovine Milk", Journal of Dairy Research, 52:255-266 (1987).
Chemical Abstract 86(9):157, Feb. 28, 1977.
Chemical Abstract 76(7):119, Feb. 14, 1992.
H. Szelag et al. "Molecular Distillation of Selected Fatty Acid Derivatives", SÖFW—Journal, 121:444-448, Jahrgang (Jun. 1995).
H. Szelag et al. "Fractionation of Ethoxylated Fatty Acids, Using Molecular Distillation", Tenside Detergents, 21(1): 14-16 (1984).
Chemical Abstract 74(20):47, May 17, 1971.
C. Olbrich et al. "Enzymatic Degradation of SLN-Effect of Surfactant and Surfactant Mixtures", Int'l. Journal of Pharmaceutics, 180:31-39 (1999).
Chemical Abstract 66(24):9944 (1967).
Yuji Shimada et al. "Enzymatic Synthesis of Steryl Esters of Polyunsaturated Fatty Acids", Journal of the American Oil Chemists' Society, 76(6):655-770 (1999).

* cited by examiner

*Primary Examiner*—Barbara P. Badio
(74) *Attorney, Agent, or Firm*—Norris McLaughlin & Marcus PA

(57) ABSTRACT

According to the present invention, there is provided a process for enzymatically producing dietary sterol fatty acid esters having physiological activities from phytosterols and fatty acids or oils and fats using lipase as a catalyst; the synthetic reaction conditions and the purification steps are so structured that dietary sterol fatty acid esters superior in sensory qualities including color, odor and taste, and safety, which is applicable as a general food, a health food or pharmaceuticals can be produced.

25 Claims, 2 Drawing Sheets

PROCESS FOR PRODUCING EDIBLE STEROL FATTY ACID ESTERS

This application is a 371 of PCT/JP01/08378 filed Sep. 26, 2001.

TECHNICAL FIELD

The present invention relates to a process for enzymatically producing a physiological active sterol fatty acid esters from phytosterols and free fatty acids using lipase as catalyst, wherein dietary sterol fatty acid esters which are excellent as a food from a view point of sensory properties and safety is obtained.

The present invention relates also to a process for producing a dietary sterol fatty acid ester of high quality from phytosterols and fats and oils having triacylglycerol as a main component.

BACKGROUND ART

Sterols such as β-sitosterol, which are obtained as a part of non-saponified products in the refining process of vegetable oils such as soybean oil and rapeseed oil, have been known to have an action for lowering the blood serum cholesterol level. As it has recently become evident that β-sitostanol, a saturated form of β-sitosterol, has a more powerful blood serum cholesterol lowering effect than β-sitosterol, it has been receiving increasing attention.

However, since the above-mentioned free sterols and free stanols are insoluble in the micellar phase in a digestive organs, these forms are hardly appropriate for their intake to develop their physiological effects. In order to improve the fat-solubility thereof, it has been proposed to ingest them in the form of sterol fatty acid esters, and recently, it has been attempted to add sterol fatty acid esters to various food products such as margarine with phytosterols, and some of them are commercially available.

By the way, sterol fatty acid esters have hitherto not been used in foods, but used in a cholesteric liquid crystal and as a hydrophilic base material for pharmaceuticals and cosmetics.

Therefore, the sterol fatty acid esters have been produced by chemical synthesis with an acid or base catalyst. In chemical synthesis, however, the reaction is generally conducted under severe conditions; therefore several problems may arise such as degraded quality of a product and generation of undesirable by-products. In addition to that, the product might be contaminated with the by-products and the reaction catalyst. It has been unavoidable to employ highly complicated purification steps after the synthetic reaction.

In this context, the use of an enzyme such as cholesterol esterase and lipase has been recently studied.

Cholesterol esterase and lipase are both categorized as one of carboxylic acid ester hydrolases and cholesterol esterase is defined as an enzyme, which generates a free sterol and a free fatty acid from a cholesterol fatty acid ester through hydrolysis.

Lipase (which usually means triacylglycerol lipase) is defined as an enzyme, which can generate glycerol and free fatty acids from glycerol fatty acid esters through hydrolysis.

Incidentally, many enzymes are found that the enzymes have both cholesterol esterase activity and lipase activity (see D. Lombardo et al.: Biochem. Biophys. Acta., 527, (1978), 142–149, D. Lombardo et al.: Biochem. Biophys. Acta, 611 (1980), 136–146, 147–155), and even now not a few examples are known which cannot be distinctly classified whether cholesterol esterase or lipase.

The above-mentioned enzymes are known to be capable of catalyzing the hydrolysis reaction of carboxylic acid ester in common cases and, on the other hand, also capable of catalyzing the synthetic reaction of ester.

Lawrence A. et al. indicated that sterol ester hydrolase derived from canine pancreatic juice, which is known as cholesterol esterase, may catalyze the synthesis of cholesterol oleic acid esters from free cholesterols and free oleic acids (Biochem. Biophys. Acta., 231 (1971) 558–560.

D. Lombardo et al. also indicated that cholesterol esterase derived from human pancreatic juice is capable of catalyzing the synthesis of cholesterol fatty acid esters (Biochimie et al., 1980, 62, 427–432).

Myojo et al. confirmed that lipase is capable of catalyzing the synthesis of cholesterol fatty acid esters (JP 5-33712 B1).

As shown above, it has been indicated that cholesterol fatty acid esters can be synthesized using enzymes as opposed to the afore-mentioned chemical synthesis.

However, all of the conventional production examples mentioned above are referring only to the synthetic reaction for sterol fatty acid esters as a general chemical product, and are not intended for the production of sterol fatty acid esters for use as general foods, health foods or pharmaceuticals. In other words, with respect to the synthetic reaction conditions and the subsequent purification process, no consideration is given for achieving good sensory qualities including color, odor and taste, and safety of the sterol fatty acid esters, which are important factors for general foods, health foods and pharmaceuticals.

Therefore, it has been difficult to employ the sterol fatty acid esters produced in the conventional process for foods and the like.

The above-described problem exists not only in the production wherein free fatty acids is employed as the fatty acids, but also in the production wherein fats and oils containing triacylglycerol as the main component are employed as starting materials.

DISCLOSURE OF THE INVENTION

Accordingly, a first object of the present invention is to provide a process for enzymatically producing a physiological active dietary sterol fatty acid esters from phytosterol derived from vegetable and free fatty acids using lipase as a catalyst, in which synthetic reaction conditions and the subsequent purification process are so constructed that the resulting dietary sterol fatty acid ester is superior in sensory properties including color, odor, and taste, and safety, and is capable of being employed as general foods, health foods or pharmaceuticals.

A second object of the present invention is to provide a process for producing dietary sterol fatty acid esters which is also superior in qualities as those described above, from phytosterols and fats and oils containing triacylglycerol as the main component, as starting materials.

The present invention for achieving the above-mentioned first object is characterized by a process for enzymatically producing a physiologically active dietary sterol fatty acid esters from phytosterols and free fatty acids using lipase as a catalyst, in which synthetic reaction conditions and the subsequent purification process are so constructed and consideration is given for achieving good sensory qualities including color, odor and taste and also safety, that the resulting dietary sterol fatty acid ester can be employed as general foods, health foods or pharmaceuticals.

That is, phytosterols and free fatty acids are used as starting materials, sterol fatty acid esters synthetic reaction is carried out under strictly controlled reaction conditions using lipase as a catalyst, and purification process in several stages is carried out to assure the superior quality of the product as a food, thereby a dietary sterol fatty acid ester which is expected to have physiological activities is enzymatically produced.

The invention is characterized by a process for enzymatically producing a physiologically active dietary sterol fatty acid esters from phytosterols and fatty acids using lipase as a catalyst, wherein fatty acids obtained by enzymolysis or high pressure continuous decomposition process are used as the fatty acid source, and synthetic reaction of sterol fatty acid esters by lipase is carried out in a system with controlled temperature and water content for a predetermined time period, followed by enzyme deactivation treatment, dehydration treatment and enzyme protein removal treatment, then unreacted sterols and fatty acids are removed by molecular distillation, coloring components are removed by treatment with an adsorbent, odorous components are removed by steam distillation, thereby a dietary sterol fatty acid ester of high quality from a view point of sensory properties and safety is obtained.

Another aspect of the invention is characterized in that water content is controlled to be 50% or less when the synthetic reaction of sterol fatty acid esters is carried out by lipase.

Another aspect of the invention is characterized in that the synthetic reaction of sterol fatty acid esters is carried out using mesophilic lipase, and in this case, the reaction is carried out at temperature between 30° C. to 50° C., and completed within 48 hours.

Another aspect of the invention is characterized in that the synthetic reaction of sterol fatty acid esters is carried out using thermostable lipase, and in this case, the reaction is carried out at temperature between 50° C. and 90° C., and completed within 24 hours, besides a substance capable of preventing the inactivation of an enzyme is added when the synthetic reaction of sterol fatty acid esters is carried out by lipase, and further a substance having anti-oxidant action is added when the synthetic reaction of sterol fatty acid esters is carried out by lipase.

Another aspect of the invention is characterized in that a molecular distillation apparatus is employed for removing unreacted sterols and fatty acids by molecular distillation treatment, and the molecular distillation is carried out under a pressure of 13.3 Pa or lower at a temperature of 150 to 250° C., and the molecular distillation is repeated several times.

Another aspect of the invention is characterized in that coloring components are removed by treatment with activated clay as an adsorbent agent, which is used in an amount of 0.1 to 50 wt % based on the weight of the materials to be treated, in the presence of an organic solvent such as hexane.

Another aspect of the invention is characterized in that odorous components are removed by steam distillation, in which the steam distillation is performed at 1330 Pa or lower and at 100 to 150° C. to prevent the production of trans fatty acids.

Another aspect of the invention is characterized in that the sterol fatty acid esters obtained as the end product has sterol fatty acid esters content of 90 wt % or more, the peroxide value of 15 or lower, the acid value of 3 or lower and a color scale (Gardner) of 6 or lower and is almost odorless as determined by a sensory test.

Another aspect of the invention is characterized in that lipase is added in a step-wise manner.

Another aspect of the invention is characterized in that when sterol fatty acid esters are used for food, it is used in the form where the sterol fatty acid esters are previously mixed with fats and oils containing triacylglycerol as the main component.

The above-mentioned invention (which corresponds to the first aspect of the invention with relation to the after-mentioned first Embodiment) will be explained in connection with FIG. 1.

According to the present invention, sterols used as starting materials (refined sterol, step 100) may be any sterol as far as it is phytosterols derived from vegetables such as soybean and rapeseed, and examples thereof include β-sitosterol, campesterol, brassicasterol, stigmasterol and choresterol. In addition to that, stanols such as β-sitostanol, a saturated form of β-sitosterol, can be employed as well. These sterols and stanols may be in the form of free sterols and free stanols or in the form of an ester in which they are bonded with other substances.

As for fatty acids (free fatty acid, step 102), any saturated fatty acid or unsaturated fatty acid having one or plural double bonds, having 4 to 32 carbon atoms and derived from an animal or a vegetable, can be used. Examples thereof include myristic acid, palmitic acid, stearic acid, oleic acid, linoleic acid, α-linolenic acid, γ-linolenic acid, arachidonic acid, eicosapentaenoic acid, docosapentaenoic acid, and docosahexaenoic acid. Typically straight-chain fatty acids are employed in the most cases, but branched-chain fatty acids can be employed as well.

According to the present invention, it is recommendable to employ fatty acids, which are obtained by enzymatic decomposition or continuous high pressure decomposition process, to obtain sterol fatty acid esters suitable for a food.

Next, the synthetic reaction of sterol fatty acid esters (step 104) and the resulting product thereof (step 106) will be explained.

In the present invention, the lipase to be used as a catalyst for the synthetic reaction of sterol fatty acid esters may be any lipase derived from various microorganisms, animals and plants. The lipase derived from a microorganism include, for example, those derived from microorganisms of the genera *Candida, Alcaligenes, Mucor, Rhizopus, Pseudomonas* and *Geotricum*.

The lipase derived from an animal include, for example, those originated from porcine pancreas. It is preferable to use lipase derived from *Candida cylindracea*. When the synthetic reaction is performed under high temperature conditions, thermostable lipase may be used as well.

The enzyme may be used in the purified or partially purified form. In the case where lipase derived from microorganism is employed, either the microorganism cell bodies or a culture of the microorganism may be used. The above-mentioned enzyme may also be in the free state or be immobilized onto any of various supports such as cerite.

The enzymes used in the present invention may be any one which can catalyze the same reactions as those catalyzed by lipase. For example, cholesterol esterase is known to be capable of catalyzing the same reactions as those catalyzed by lipase, and therefore can also be used in the present invention.

The conditions employed for the synthetic reaction of the sterol fatty acid esters with lipase should be controlled strictly so that sterol fatty acid esters having qualities not only suitable for a food such as sensory properties including color, odor and taste, but also assuring safety can be produced at a low cost. Hereinafter the conditions for synthetic reaction in step 104 will be explained.

The amount of the enzyme used may be 50,000 units or less, preferably 10,000 units or less, per gram of the starting material sterols. (One unit is defined as an amount of the enzyme capable of releasing 1 µmole of a fatty acid from olive oil in 1 minute.) To avoid the deterioration due to heat treatment in the production process and to produce a more inexpensive end product, it is desirable to use the enzyme in a smallest possible amount, preferably in an amount of 1,000 units or less per gram of the starting material sterol. In addition to that, the enzyme can also be added in a step-wise manner during the synthetic reaction to reduce the amount of the enzyme used.

The starting material sterols (step 100) and fatty acids (step 102) can be used at any ratio, however, it is preferable to have a higher ratio of fatty acids to sterols in order to improve the synthetic ratio, the ratio of fatty acids to sterols is preferably 50% or higher. As sterols are solid at a normal temperature, a desirable weight ratio of fatty acids to sterols is 100% or higher in order to further improve the workability during the production process. Furthermore, as starting material costs and production costs should be reduced for obtaining a more inexpensive product, the use ratio of fatty acids to sterols of 100 to 500% may be preferred.

The sterols and fatty acids, as starting materials, can be directly mixed and supplied to the synthetic reaction, however, a small amount of water may be added in order to raise the synthetic ratio. On the other hand, as the water added must be removed in the purification process after the synthesis of the sterol fatty acid esters, the amount of the water used must be as small as possible, for reducing the production cost, and is preferably up to 50% based on the weight of the starting material sterols.

To minimize the thermal degradation during the reaction, the reaction is preferably performed at a lower temperature for a shorter time period, desirably at 30 to 50° C. within 48 hours. When the synthesis is performed at a low temperature, a lipase which can readily exert its enzymatic activity at such a low temperature is preferably used.

On the other hand, as sterols, one of the starting materials, have very high melting points, they tend to have poor compatibility with the other starting material, fatty acids, and that may lead to low synthetic reaction efficiency of the sterol fatty acid esters by lipase. To overcome this problem, the synthetic reaction can be performed at higher temperature, preferably at 50 to 90° C. using thermostable lipase. In this case, however, thermal deterioration of sterol fatty acid esters may proceed more aggressively or lipase may be inactivated during the reaction, therefore, a substance having anti-oxidant effect such as Vitamin E and tea polyphenol may be added to prevent the thermal or oxidative deterioration of the sterol fatty acid esters, and a substance capable of preventing the inactivation of an enzyme, including a salt such as bile salts, a carbohydrate and a protein may be added to prevent the inactivation of the enzyme.

To enhance the efficiency of the synthetic reaction, the reaction is usually carried out with stirring, but in some cases, it can be carried out in a static state. When the reaction is performed in a static state, an emulsifying agent or the like may be added. An organic solvent such as hexane may also be used to enhance the efficiency of the reaction, but in this case, the solvent must be removed, which may increase the production cost.

The purification of sterol fatty acid esters will be illustrated hereinbelow.

In the present invention, in order to achieve inexpensive production of sterol fatty acid esters which are superior in qualities suitable for a food including color, odor and taste, also in safety, the above-mentioned purification process after the synthetic reaction must be performed carefully.

At first, after the synthetic reaction of the sterol fatty acid esters is completed, inactivation of the enzyme, dehydration and removal of the enzyme protein are performed. The inactivation of the enzyme is achieved by stirring at 60° C. or higher for about 30 to 120 min. The dehydration is performed by treatment at 60° C. or higher for a predetermined time period under reduced pressure. The removal of the enzyme protein can be achieved by filtration using a conventional filter paper, filter cloth or a filtration filter. If the removal of the enzyme protein by the filtration is insufficient, then deterioration in quality such as coloration may be caused by the heating in subsequent processes. Therefore, the enzyme protein must be removed completely. For more effective removal, a filter aid such as diatomaceous earth can be previously added, and then stirred and filtered. So far, we have explained the treatment up to step 106.

After the removal of the enzyme protein (step 106), the sterol fatty acid esters still contain unreacted sterols, fatty acids, coloring components, and odorous components.

Therefore, according to the present invention, molecular distillation (step 110) is next performed to remove the sterols and fatty acids (step 108) efficiently.

During this process, the end product, the sterol fatty acid ester, is obtained as the residue (step 112) and unreacted sterols and fatty acids, and a part of coloring components and odorous components are obtained as a fraction (step 108).

As the apparatus for the molecular distillation, any type can be used which is selected from falling film type, centrifugal type or any other type of short pass distillation apparatus. The molecular distillation is preferably performed at 133 Pa or lower and at 100 to 300° C., more preferably at 13.3 Pa or lower and at 150 to 250° C. The molecular distillation may be performed repeatedly several times.

Subsequently, treatment with an adsorbent is performed to remove coloring components and the like. This is because sterol fatty acid esters (residue) after the molecular distillation contains coloring components derived from the starting materials, coloring components resulting from the heating during the distillation, and odorous components and the like (step 112).

To remove the coloring components (step 114) efficiently according to the present invention, sterol fatty acid esters are treated with an adsorbent (step 116). The adsorbent used in this case includes those typically used for purification of fats and oils, such as activated clay, acidic clay, activated carbon, silica, silica-magnesia and so on, but activated clay is preferred. The adsorbent is preferably added in an amount of 0.1 to 50 wt %, more preferably 1 to 20 wt %, based on the weight of the starting material to be treated. For more efficient decoloring, it is preferred to employ activated carbon in a non-polar solvent such as hexane. The solvent is preferably used in an amount of 0.1 to 50 times, more preferably 0.5 to 20 times that of the starting material to be treated. When an organic solvent is employed, the solvent must be removed after the treatment with the adsorbent. The treatment with the adsorbent can be repeated for several times.

As the final step, steam distillation (step 122) is performed to remove odorous components (step 120) and the like. Odorous components (step 120) derived from the starting materials or generated in the preceding steps must be removed from sterol fatty acid esters obtained after the decoloring (step 118), in order for sterol fatty acid esters to be used as a food. When the decoloring is performed using an organic solvent, the organic solvent may remain in the product even after the solvent removal treatment, therefore, such organic solvent must be removed completely. Steam distillation treatment (step 122) makes it possible to remove the above-mentioned odorous components (step 120) and the remaining organic solvent. In the steam distillation, any type of apparatus may be used, including those of continuous type, semi-continuous type and batch type. It is desirable to perform the steam distillation under the conditions of 13.3 kPa or lower and 50 to 250° C., preferably 1330 Pa or lower and 100 to 150° C. By lowering the temperature, the production of trans fatty acids can be prevented. The steam distillation may be repeated several times.

The obtained sterol fatty acid esters (step 124) can be used as a food as it is; however, because of extremely poor fluidity and workability, sterol fatty acid esters are preferably used in the form where it is previously mixed with other fats and oils, such as those containing triacylglycerol as the main component. In this case, any mixing ratio may be employed depending on the intended use, but it is desirable to mix the fat and oil in an amount of 30 to 300 wt % based on the weight of sterol fatty acid esters in order to improve the workability. As the fats and oils containing triacylglycerol as the main component, food fats and oils, such as soybean oil and rapeseed oil may be used. Instead of the fats and oils containing triacylglycerol as the main component, other fats and oils containing other components such as diacylglycerol may also be used.

The sterol fatty acid esters obtained as the end product according to the present invention, is almost tasteless, odorless and pale yellow in color and is superior in safety, and therefore has qualities suitable for a general food, a health food and pharmaceuticals. The sterol fatty acid esters have the potential effect of reducing cholesterol level. Accordingly, the sterol fatty acid esters are expected to be used, not only as a functional material, in a general food product including margarine and dressing, but also in a health food product, or in a pharmaceuticals and the like.

As described heretofore, according to the present invention, a synthetic reaction of sterol fatty acid esters is carried out under strictly controlled reaction conditions, employing phytosterols and fatty acids as starting materials, and employing lipase as a catalyst, and carrying out purification treatment in several steps following the synthesis, to obtain a quality product for use as a food, thereby providing specific advantages of the present invention, that is dietary sterol fatty acid esters of high physiological activities and high quality can be produced.

In contrast to the present invention, prior art (for example JP 5-33712 B1) describes production of sterol fatty acid esters by use of enzymatic activity as well.

However, the production process described in prior art is not aiming at production of the dietary sterol fatty acid ester.

Therefore, there are the following differences between the production process described in prior art and the present invention.

(a) In the prior art, it is described that fatty acids having 2 to 32 carbon atoms can be used as the starting material fatty acids, but according to the present invention, the starting materials are those obtained by enzymolysis or continuous high pressure decomposition process.

Therefore, according to the present invention, there is the advantage that the deterioration of the starting material fatty acids is little and a product of high safety as a food can be produced.

(b) In the prior art, it is described that lipase or cholesterol esterase can be employed, while in the present invention, the enzyme is added in a step-wise manner.

Therefore, the deactivation of the enzyme during the reaction process can be reduced in the present invention and the amount of the enzyme used can be decreased. Therefore there is another advantage that the product can be obtained at low cost.

(c) According to the present invention, a substance which inhibits the inactivation of an enzyme is added or a substance which has anti-oxidant action is added while the synthetic reaction of the sterol fatty acid esters is carried out by lipase; however, there is no such description in the prior art.

(d) In the prior art, extraction with an ether, or column chromatography process are described for removal of unreacted free fatty acids or free sterols; however, ethers cannot be used for production of a food, and the column chromatography process increases the cost.

On the contrary, in the present invention, unreacted free fatty acids and free sterols are removed by molecular distillation. Therefore, there is the advantage that products can be obtained safely at a low cost.

(e) In the prior art there is no description of construction for removing coloring components and odorous components. Therefore, the resulting product cannot be used for a food.

On the contrary, in the present invention, treatment with an adsorbent is carried out for removal of coloring components, and steam distillation is carried out for removal of odorous components. Therefore, it has the advantage that a food which is superior in sensory properties including color, odor and taste, and safety can be produced.

As described above, when the present invention is compared with the prior art, the present invention has advantages specific to the present invention, that sterol fatty acid esters for a food can be produced safely and at a low cost.

Next, the second aspect of the present invention in order to achieve the above-mentioned second object will be explained in connection with FIG. 2.

The present invention to achieve the above-mentioned second object is characterized in that quality dietary sterol fatty acid esters are produced from sterols derived from vegetable and a fat and oil containing triacylglycerol as the main component as starting materials.

That is a synthetic reaction of sterol fatty acid esters is carried out under strictly controlled reaction conditions, by employing phytosterols and fats and oils containing triacylglycerol as the main component as starting materials, and by employing an enzyme having a lipolytic activity, as a catalyst, and by carrying out purification treatment in several steps following the synthesis, to obtain a dietary sterol fatty acid ester of high quality enzymatically.

Another aspect of the invention is characterized by a process for producing dietary sterol fatty acid esters comprising;

carrying out a synthetic reaction of sterol fatty acid esters by employing phytosterols and a fat and oil containing triacylglycerols as the main component, as starting material, and by employing an enzyme having a lipolytic activity in a system with controlled temperature and water content for a predetermined time period, then performing enzyme deactivation treatment, dehydration treatment and enzyme protein removal treatment, performing as a first purification step, molecular distillation to primarily remove unreacted sterols and fatty acids;

performing as a second purification step, treatment with an adsorbent to primarily remove coloring components; and performing as a third purification step, steam distillation to primarily remove odorous components, to obtain sterol fatty acid esters being superior in safety and sensory properties for food.

Another aspect of the invention is characterized in that phytosterols composition used as the starting material contains β-sitosterol in an amount of 20 to 80% by weight.

Another aspect of the invention is characterized in that the fat and oil containing triacylglycerol as the main component which is used as the starting material is any one of oils selected from soybean oil, rapeseed oil, and olive oil, and used alone or in admixture or two or more kinds.

Another aspect of the invention is characterized in that an enzyme having a decomposition activity of sterol fatty acid esters is employed as the enzyme having a lipolytic activity.

Another aspect of the invention is characterized in that an enzyme having a decomposition activity of triacylglycerol is employed as the enzyme having a lipolytic activity.

Another aspect of the invention is characterized in that the enzyme having an activity of decomposing triacylglycerol is cholesterol esterase or lipase.

Another aspect of the invention is characterized in that the synthetic reaction of sterol fatty acid esters by an enzyme having a lipolytic activity is carried out for a predetermined time period, in a system with controlled temperature and water content, in which the reaction is carried out under conditions of water content of 0.1 to 50% based on the weight of the starting materials, at 30 to 60° C., and within 48 hours.

Another aspect of the invention is characterized in that the synthetic reaction of sterol fatty acid esters by an enzyme having a lipolytic activity is carried out for a predetermined time period, in a system with controlled temperature and water content, wherein a thermostable lipolytic enzyme is employed and the reaction is carried out in the presence of a substance which prevents inactivation of the enzyme and a substance which has an anti-oxidant action, under conditions of the water content of 0.1 to 50% by weight based on the weight of the starting materials, at 50 to 90° C., and within 48 hours.

Another aspect of the invention is characterized in that a lipolytic enzyme originated from a microorganism of the genus Rhizopus is employed as the thermostable lipolytic enzyme.

Another aspect of the invention is characterized in that the molecular distillation treatment, as the first purification step, is carried out at 13.3 Pa or lower and at 100 to 250° C. for removing primarily unreacted sterols and fatty acids.

Another aspect of the invention is characterized in that the treatment with an adsorbent for removing primarily coloring components, as the second purification step, is carried out by using activated clay in an amount of 0.1 to 50% based on the weight of the materials to be treated and at 100° C. or lower.

Another aspect of the invention is characterized in that the steam distillation treatment, as the third purification step, is carried out at 1330 Pa or lower and 50 to 150° C. to remove odorous components, at the same time to prevent the generation of trans fatty acids.

Another aspect of the invention is characterized in that the end product sterol fatty acid ester has a sterol fatty acid ester content of 90 wt %o or more, a peroxide value of 15 or lower, an acid value of 3 or lower and a color scale (Gardner) of 6 or lower and is almost odorless as determined by a sensory test.

Then the above-mentioned invention (which corresponds to the second aspect of the invention with relation to the after-mentioned second Embodiment) will be explained in connection with FIG. 2.

Phytosterols (purified sterol, step 200), one of the starting materials according to the present invention, include any sterols which is derived from a vegetable such as soybean and rapeseed, and examples thereof include β-sitosterol, campesterol, brassicasterol, stigmasterol, and cholesterol, and stanols such as β-sitostanol, a saturated form thereof can be employed as well. These sterols and stanols can be used in free form or in ester form in which they are bonded to other substances.

The other starting material, i.e. the fats and oils containing triacylglycerol as the main component (triacylglycerol, step 202) includes vegetable-derived oils such as soybean oil, rapeseed oil, olive oil, palm oil, sunflower seed oil, safflower oil, corn oil, cotton seed oil, sesame oil, rice bran oil, coconut oil, and peanut oil, and these oils may be used singly or in admixture of two or more kinds. The fats and oils may be added in an amount of 50 to 500 wt %, preferably 100 to 300 wt %, based on the weight of the sterol-containing fraction.

Then the synthetic reaction of the sterol fatty acid esters in the present embodiment and the resulting product will be explained in connection with steps 204 and 206.

The lipolytic enzyme to be used as a catalyst for the synthetic reaction of the sterol fatty acid esters (step 204) may be any of those originated from various microorganisms, animals and plants. The enzyme having a lipolytic activity originated from a microorganism include, for example, those from microorganisms of the genera *Pseudomonas, Alcaligenes, Candida, Mucor, Rhizopus* and *Geotricum*. The enzyme having a lipolytic activity originated from an animal include, for example, those originated from porcine pancreas.

The enzyme used in the present invention is preferably one capable of degrading sterol fatty acid esters or one capable of degrading triacylglycerol, and concrete example thereof includes cholesterol esterase and lipase. The former enzyme includes those originated from a microorganism of genus *Pseudomonas*, and the latter enzyme includes those originated from a microorganism of genera *Alcaligenes* and *Candida*.

A number of enzymes having both an activity of degrading sterol fatty acid esters and an activity of degrading triacylglycerol have been also known, and according to the present invention, any lipolytic enzyme which is able to catalyze the synthetic reaction of sterol fatty acid esters can be used without concern for enzyme-classificatory constrains.

When the synthetic reaction of sterol fatty acid esters is performed under high temperature conditions, a thermostable lipolytic enzyme may be used. As the thermostable lipolytic enzyme, those originated from a microorganism of genera *Rhizopus* is preferred. The enzyme may be used in the purified or partially purified form. When a lipolytic enzyme originated from a microorganism is employed, either the microorganism cell bodies themselves or the culture of the microorganism may be used. The enzyme may also be in the free state or be immobilized onto any of various supports such as cerite.

The conditions to be employed for the synthetic reaction of the sterol fatty acid esters with a lipolytic enzyme according to the present invention, should be controlled strictly so that sterol fatty acid esters having qualities not only suitable for a food, such as sensory properties including color, odor and taste, but also assuring safety, can be produced at a low cost. The synthetic reaction conditions for step 204 will be described in the following.

The enzyme may be used in an amount of 50,000 units or less, preferably 10,000 units or less per gram of the starting material sterols. (One unit is defined as an amount of the enzyme capable of releasing 1 μmole of a fatty acid from olive oil in 1 minute.) To avoid the deterioration of the enzyme caused by the treatment under heating in the production process and to produce the end product at lower cost, it is desirable to use the enzyme in a smallest possible amount, preferably in an amount of 1,000 units or less per gram of the starting material sterols. The enzyme can also be added in a step-wise manner during the synthetic reaction to reduce the amount of the enzyme.

In the present invention, to prevent triacylglycerol, diacylglycerol or monoacylglycerol from remaining after the synthetic reaction of the sterol fatty acid esters, it is preferred to perform the enzymatic reaction by previously adding water in an amount of 0.1 wt % or more. By performing the enzymatic reaction in the presence of water of 0.1 wt % or more, triacylglycerol, and coexisting trace amount of diacylglycerol and monoacylglycerol and the like are subjected to hydrolysis reaction and decomposed into free fatty acids and glycerol, and these fatty acids generated by the decomposition also become substrates for the ester synthetic reaction of the sterol fatty acid esters. The efficiency of the synthetic reaction can be enhanced, by increasing the amount of the water added. On the other hand, since the added water must be removed in the purification process after the synthesis of the sterol fatty acid esters, the amount of water should be minimized for lowering the production cost, and a desirable amount is 300% or less, preferably 50% or less, based on the weight of the starting materials.

To minimize the thermal degradation of the product during the synthetic reaction, the reaction is preferably performed at lower temperature for shorter time period, usually at 30 to 50° C. within 48 hours. When the synthesis is performed at lower temperature, lipolytic enzyme which can readily exert its enzymatic activity at such lower temperature is preferably used.

On the other hand, sterols, constituting one main starting material, have very high melting points thereby their compatibility with the other substrate, i.e. fats and oils containing triacylglycerol as the main component, is extremely poor, and in some cases, the efficiency of the synthetic reaction of the sterol fatty acid esters by the lipolytic enzyme becomes low. To overcome this problem, the synthetic reaction can be performed at higher temperature, preferably at 50 to 80° C. within 24 hours using thermostable lipolytic enzyme. In this case, however, thermal deterioration may proceed more aggressively or the enzyme may be inactivated during the reaction, a substance having anti-oxidant effect, such as Vitamin E and tea polyphenol, may be added to prevent the thermal or oxidative deterioration of the sterol fatty acid esters, and a substance capable of inhibiting the inactivation of the enzyme, such as a salt including a bile salt, a carbohydrate and a protein, may be added to prevent the inactivation of the enzyme.

To enhance the efficiency of the synthetic reaction, the present reaction is usually performed while stirring, but in some cases it may be performed in a static state. When the reaction is performed in a static state, an emulsifying agent or the like may be added. An organic solvent such as hexane may also be used to enhance the efficiency of the reaction, but in this case, the solvent must be removed, and that may increase the production cost.

After the synthetic reaction of the sterol fatty acid esters is completed, inactivation of the enzyme, dehydration and removal of the enzyme protein are performed. The inactivation of the enzyme is achieved by stirring at 60 to 100° C. for about 30 to 120 min. The dehydration treatment is performed at 60 to 120° C. for a predetermined time period under reduced pressure. The removal of the enzyme protein can be achieved by filtration using a conventional filter paper, filter cloth or a filtration filter; however, in case the removal of the enzyme protein is insufficient, deterioration of the product in quality such as coloration may likely be caused by the heating in subsequent processes, therefore, the enzyme protein must be removed completely. For more effective removal, a filter aid such as diatomaceous earth and clay can be previously added and then stirred and filtered. So far is the treatment up to step 206.

Next, the purification process for the sterol fatty acid esters will be explained.

According to the present invention, in order to produce sterol fatty acid esters having qualities suitable for food including color, odor and taste, and is superior in safety at low cost, the above-mentioned purification of the product after the synthetic reaction should be performed carefully.

As the sterol fatty acid esters obtained after the enzyme protein removal treatment (step 206) according to the present invention, contains unreacted sterols and fatty acids, molecular distillation, as a first purification step, is performed (step 210) to efficiently remove these substances, wherein the sterol fatty acid esters, as the end product, is obtained as a remaining fraction (Step 212), while unreacted sterols and fatty acids and parts of odorous components are removed as distillate fractions (Step 208). Examples of the apparatus for the molecular distillation include those of falling film type, centrifugal type or any other type of short pass distillation apparatus, but any apparatus may be used as long as it can achieve the desired vacuum pressure and temperature and can remove the desired free sterols, free fatty acids and other trace components. The molecular distillation is preferably performed at 133 Pa or lower and at 100 to 300° C., more preferably at 13.3 Pa or lower and at 100 to 250° C. The molecular distillation may be performed repeatedly several times. As this process allows the removal of odorous components, which cannot be completely removed in the steam distillation (Step 222), the third purification step, molecular distillation treatment (step 210) is required to be performed prior to the steam distillation (Step 222) to produce an end product from which odorous components are efficiently removed.

Subsequently, in a second purification step, coloring components (Step 214) are primarily removed. The sterol fatty acid esters after the molecular distillation (Step 212) contains coloring components derived from the starting materials and coloring components resulting from the heating during the molecular distillation (step 214), as well as odorous components (step 220). According to the present invention, to remove the coloring components efficiently, treatment with an adsorbent (Step 216) is performed.

The adsorbent used in this case includes those adsorbents conventionally used for purification of fats and oils, such as activated clay, acidic clay, activated carbon, silica, silica-magnesia and so on, and the use of activated clay, activated carbon or silica is preferred. These may be used singly or in admixture of two or more kinds. The adsorbent is preferably added in an amount of 0.1 to 50 wt %, more preferably 1 to 20 wt %, based on the weight of the material to be treated. For more efficient decoloring, the treatment can be carried out with the above-mentioned adsorbent in a non-polar solvent such as hexane. The solvent is preferably used in an amount of 0.1 to 50 times, more preferably 0.5 to 20 times (by weight), that of the material to be treated. When a non-polar solvent is not used, the decoloring is performed by adding the adsorbent followed by stirring at 40 to 150° C. for a predetermined time period. This procedure may be performed under normal atmospheric pressure, but the procedure is preferably performed under reduced pressure to prevent the material from deterioration and to carry out more efficient decoloring. A lower pressure is preferred, such as 13.3 kPa or lower. After the treatment, the adsorbent is removed by filtration using any conventional filtrating means, such as a filter paper, filter cloth or a filtration filter. For more effective removal, a filter aid such as diatomaceous earth can be added prior to the filtration and then stirred and filtered. In the case where a non-polar solvent is used, it is preferred to dissolve the material to be treated in the non-polar solvent previously, and then add the adsorbent thereto and stir the resulting reaction mixture at 0 to 60° C. for a predetermined time period.

The adsorbent is removed in the same manner as stated above, and then the non-polar solvent is removed by distillation (step 222). When the more complete removal of the coloring components is required or the material to be discolored has darker color, it is preferred to repeat the treatment with the adsorbent several times. When the treatment is repeated, additional any adsorbent may be added after the filtration of the preceding adsorbent and then another round of procedure is performed in the same manner. When a non-polar solvent is used, additional any adsorbent may be added after the proceeding round of addition of an adsorbent, stirring and filtration without the need of removal of the solvent, and then the subsequent round is performed. The solvent is removed after filtration in the final round is completed.

The material may be treated with an acid or alkali prior the treatment with the adsorbent, thereby achieving the decoloring more effectively. In this case, the material to be treated may be dissolved in a non-polar solvent such as hexane to make the material in a micellar state, and then treated with an acid or alkali. As in this step, additional odorous components may be generated or attached to the sterol fatty acid esters, the treatment with the adsorbent (Step 216) is required to be performed after the molecular distillation (Step 210) and prior to the steam distillation (Step 222).

Finally as the third purification step, steam distillation (Step 222) is performed to remove odorous components (Step 220) and the like. For use as a food, the sterol fatty acid esters after the decoloring is required to be free from odorous components derived from the starting material or generated in the preceding steps. When the decoloring is performed using an organic solvent, the organic solvent may remain in the product even after the removal treatment of the solvent. Therefore, the remaining organic solvent must be removed completely. According to the steam distillation, the odorous components and the organic solvent remaining in the product can be almost completely removed.

In the steam distillation, any type of apparatus that is selected from continuous type, semi-continuous type and batch type apparatus can be used. The steam distillation is desirable to be performed under the conditions of 13.3 kPa or lower and 50 to 200° C., preferably 1330 Pa or lower and 50 to 150° C. The steam distillation at lower temperature is advantageous as it can prevent generation of trans fatty acids. The steam distillation may be repeated several times. As stated previously, in order to completely remove the odorous components that cannot be removed only through the steam distillation, it is required to perform both of the steam distillation and the molecular distillation (Step 210). In this case, it is important to perform the molecular distillation (Step 210) prior to the steam distillation.

The sterol fatty acid esters (Step 224), the end product of the present invention, is almost tasteless, odorless and colorless or pale yellow in color, superior in safety, and has properties suitable for a general food, a health food and pharmaceuticals. The sterol fatty acid esters are expected to have the potential effect of reducing cholesterol level, therefore it is expected to be used, as a functional material, in general food products such as margarine and dressing and health food products and, in the future, in pharmaceuticals.

BEST MODE FOR CARRYING OUT THE INVENTION

The present invention will be described more in detail by way of the following examples. The present invention, however, is not limited to these specific examples.

Figure 1:
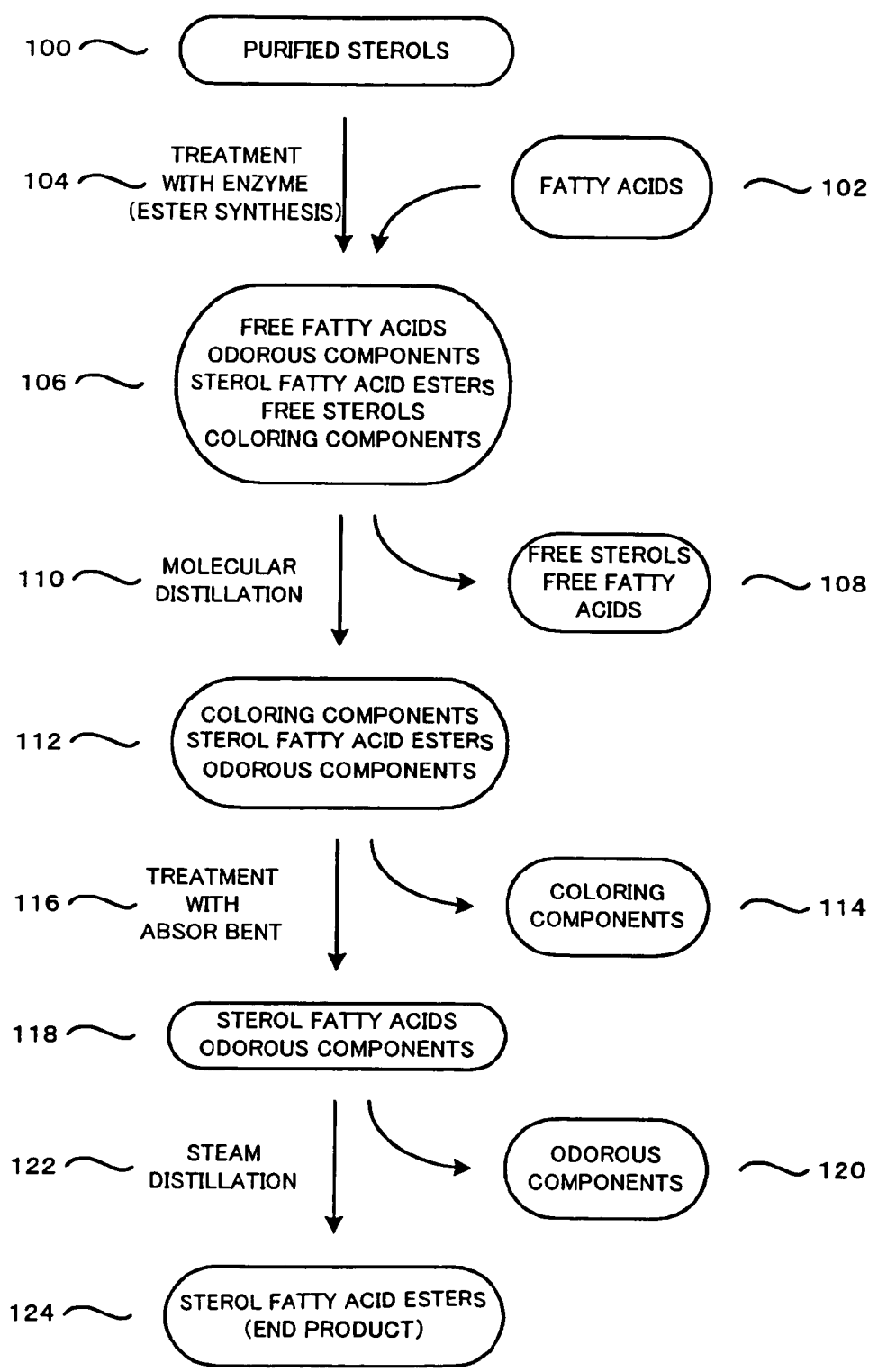
FIG. 1 is a schematic diagram illustrating a process for producing dietary sterol fatty acid esters according to the first embodiment of the present invention.

The first embodiment according to the first aspect of the present invention will be described hereinbelow. The first embodiment corresponds to the invention illustrated in the above-mentioned FIG. 1.

EXAMPLE 1

Soybean-derived sterol (sterol content: 95 wt %) (100 g) and oleic acid (oleic acid content: 99%) (200 g) were mixed at 40° C. and dissolved then lipase powder originated from a microorganism of the genus *Candida* (360,000 units/g) (2.0 g) was further added thereto while stirring the starting material mixture solution. The synthetic reaction was carried out at 40° C. for 24 hours while stirring, then the reaction mixture was heated to 80° C. and stirred at that temperature for 30 min. to inactivate the enzyme. The resulting product was added with diatomaceous earth (1.0 g), stirred, and then filtered to remove the enzyme protein. The resultant product was subjected to molecular distillation using a centrifugal molecular distillation apparatus at a vacuum pressure of 1.33 Pa, an evaporating surface temperature of 230° C. and a flow rate of 2.0 L/hr to give a sterol fatty acid ester (141 g) free from unreacted free sterols and free fatty acids. For the treatment with an adsorbent, the sterol fatty acid esters were dissolved in hexane (the amount of which was 10 times that of the residue), added with 20 wt % (based on the residue) of activated clay, and then stirred at room temperature for 30 min. The resulting solution was filtered to remove the activated clay having coloring components adsorbed thereon, and the filtrate was evaporated using an evaporator to remove the solvent, thereby giving the sterol fatty acid ester without coloring components (122 g). Finally, the sterol fatty acid esters were subjected to steam distillation using a batch-type steam distillation apparatus under the condition of vacuum pressure of 500 Pa, a distillation temperature of 150° C. and distillation time of 1 hour, thereby giving the sterol fatty acid ester without odorous components (118 g). The obtained sterol fatty acid ester was almost tasteless, odorless and pale yellow in color. The analytic results are shown in Table 1.

The sterol fatty acid esters were mixed with soybean oil in an amount of 100 wt % based on the weight of the sterol fatty acid esters, and a product having good fluidity was obtained.

EXAMPLE 2

The materials used in EXAMPLE 1, i.e. soybean-derived sterol (sterol content: 95 wt %) (100 g) and oleic acid (oleic acid content: 99%) (200 g) were mixed with 30 g of water and dissolved then lipase powder originated from a microorganism of the genus *Candida* (360,000 units/g) (2.0 g) was further added thereto while stirring the starting material mixture solution. The synthetic reaction was carried out at 40° C. for 24 hours while stirring, then the reaction mixture was heated to 80° C. and stirred at that temperature for 30 min. to inactivate the enzyme. The resulting product was added with diatomaceous earth (1.0 g), stirred, and then filtered to remove the enzyme protein. The product was dehydrated at 13.3 kPa and 80° C. with stirring for about 1 hour. Then purification was carried out in the same manner as in EXAMPLE 1 and sterol fatty acid esters (123 g) which had improved color, odor and taste was finally obtained. The obtained sterol fatty acid esters were almost tasteless, odorless and pale yellow in color. The analytic results are shown in Table 1.

EXAMPLE 3

The starting materials employed in EXAMPLE 1 were mixed and dissolved at 60° C. and thermostable lipase powder originated from a microorganism of the genus *Rhizopus* (10,000 units/g) (3.0 g) was added thereto while stirring. The synthetic reaction was carried out at 60° C. for 8 hours while stirring, then further heated to 100° C. and stirred at that temperature for 30 min. Then inactivation of the enzyme, removal of the enzyme protein were carried out in the same manner as in EXAMPLE 1. The purification was carried out in the same manner as in EXAMPLE 1 to give a sterol fatty acid ester (124 g). The obtained sterol fatty acid esters were almost tasteless, odorless and pale yellow in color. The analytic results are shown in Table 1.

EXAMPLE 4

To the starting materials employed in EXAMPLE 2 were added Vitamin E in an amount of 0.5% and bile salt of 0.2% based on the weight of the starting materials and mixed and dissolved at 60° C. and thermostable lipase powder originated from a microorganism of the genus *Rhizopus* (10,000 units/g) (3.0 g) was added thereto while stirring. The synthetic reaction was carried out at 60° C. for 8 hours while stirring, then further heated to 100° C. and stirred at that temperature for 30 min. Then inactivation of the enzyme, dehydration and removal of the enzyme protein were carried out in the same manner as in EXAMPLE 1. The purification was carried out in the same manner as in EXAMPLE 1 to give sterol fatty acid esters (127 g). The obtained sterol fatty acid esters were almost tasteless, odorless and pale yellow in color. The analytic results are shown in Table 1.

COMPARATIVE EXAMPLE 1

The starting materials employed in EXAMPLE 1 were mixed and dissolved at 50° C. and lipase powder originated from a microorganism of the genus *Candida* (360,000 units/g) (2.0 g) was added thereto while stirring. The synthetic reaction was carried out at 50° C. for 36 hours while stirring. Then molecular distillation treatment was carried out using a falling film molecular distillation apparatus followed by treatment with activated carbon and sterol fatty acid esters (82 g) were obtained. The sterol fatty acid ester had a characteristic pungent odor and was brown in color. The analytic results are shown in Table 1.

TABLE 1

|  |  | Ex. 1 | Ex. 2 | Ex. 3 | Ex. 4 | C. Ex. 1 |
|---|---|---|---|---|---|---|
| Sterol fatty acid esters content (wt %) | TLC-FID % | 96.1 | 97.5 | 98.7 | 98.9 | 95.4 |
| Peroxide value (POV) | meq/kg | 4.5 | 5.1 | 12.3 | 6.4 | 18.2 |
| Acid value (AV) | mg-KOH/g | 0.2 | 0.3 | 0.5 | 0.4 | 2.6 |
| Color | Gardner Scale | 3− | 3− | 4+ | 4− | 9+ |
| Odor | Sensory evaluation | almost odorless | almost odorless | almost odorless | almost odorless | characteristic pungent odor |
| Taste | Sensory evaluation | tasteless | tasteless | tasteless | tasteless | bitterness |
| Trans fatty acid content | GCarea % | 1.0 | 1.0 | 1.2 | 1.1 | 5.0 |

Figure 2:
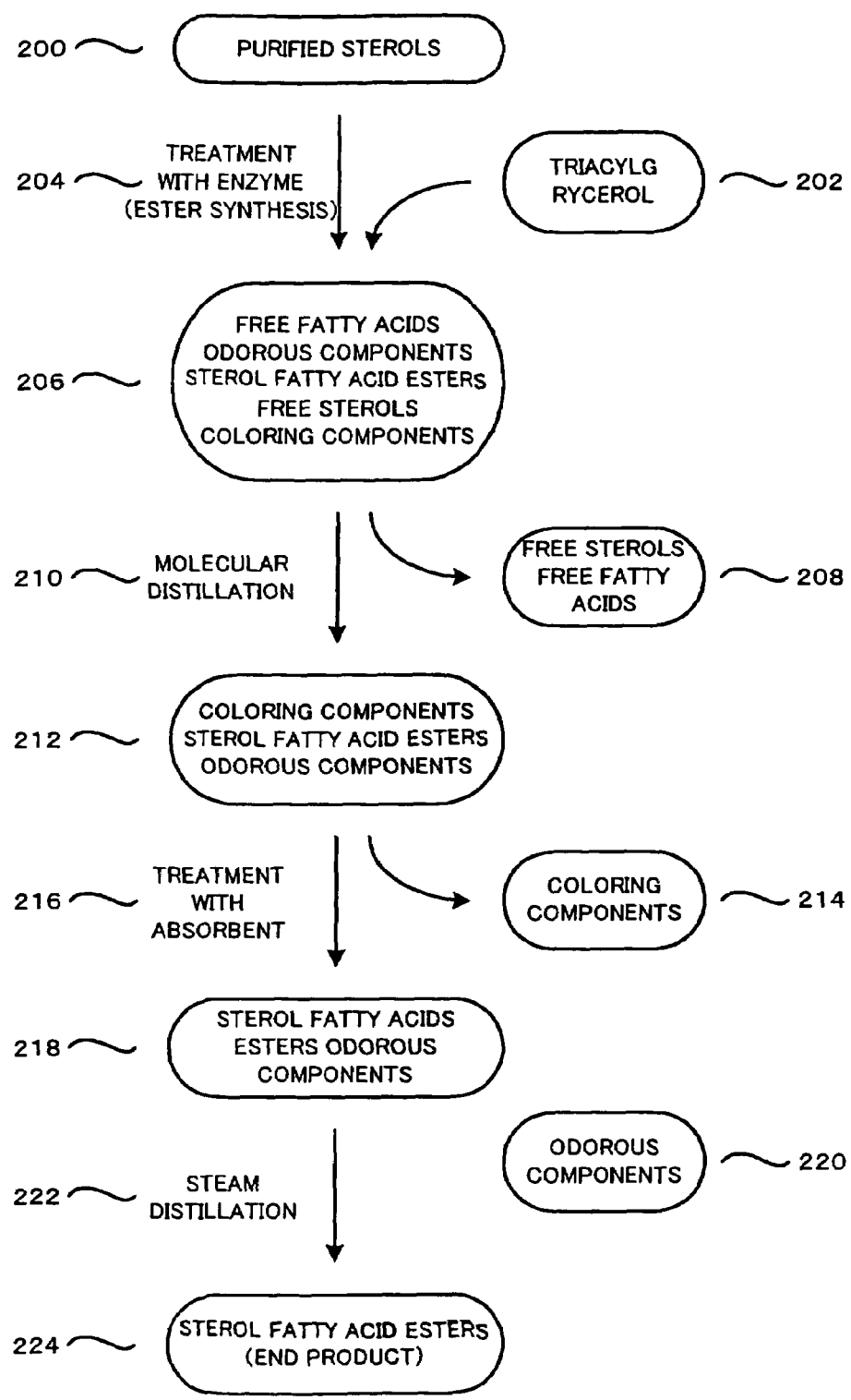
FIG. 2 is a schematic diagram illustrating a process for producing dietary sterol fatty acid esters according to the second embodiment of the present invention.

Next, second embodiment according to the second aspect of the present invention will be described. The second embodiment corresponds to the above-mentioned invention illustrated in FIG. 2.

EXAMPLE 5

Phytosterols (β-sitosterol content:42.5%) (50 g) and refined soybean oil (100 g) were mixed and a suspension in water (50 g) of lipolytic enzyme powder originated from a microorganism of the genus *Pseudomonas* (50,000 units/g) (2.0 g) having an activity of decomposing sterol fatty acid esters in water (50 g) was further added thereto, and the synthetic reaction of sterol fatty acid esters was carried out at 40° C. for 24 hours with stirring. Then the reaction mixture was heated to 80° C. and stirred at that temperature for 30 min. to inactivate the enzyme, subjected to washing with hot water, and dehydration at 80° C. under reduced pressure, then diatomaceous earth (1.0 g) was added thereto, stirred, and filtered to remove the enzyme protein.

The resultant product was subjected to first purification step, i.e. molecular distillation, using a centrifugal molecular distillation apparatus at a vacuum pressure of 1.5 Pa, an evaporating surface temperature of 230° C. and unreacted free fatty acids and sterols were removed as distillate fractions. Then, second purification step was carried out by adding activated clay in an amount of 10% based on the remaining fraction, stirring at 80° C. under reduced pressure for 30 minutes, and removing the activated clay having absorbed the coloring components by filtration. The third purification process, steam distillation, was carried out using a batch-type steam distillation apparatus under the condition of a vacuum pressure of 500 Pa, a distillation temperature of 150° C., and a distillation time of 1 hour, thereby finally giving a sterol fatty acid ester (56 g) free from odorous components.

The produced sterol fatty acid esters had a purity of 96.5%, was almost tasteless, odorless and pale yellow in color. The analytic results are shown in Table 2.

EXAMPLE 6

Phytosterols (β-sitosterol content:42.5%) (50 g) and refined rapeseed oil (100 g) were mixed and a suspension in water (50 g) of lipolytic enzyme powder originated from a microorganism of the genus *Alcaligenes* (90,000 units/g) (1.0 g) was further added thereto, and the synthetic reaction of sterol fatty acid esters were carried out at 40° C. for 24 hours with stirring. Then the reaction mixture was heated to 80° C. and stirred at that temperature for 30 min. to inactivate the enzyme, subjected to washing with hot water, and dehydration at 80° C. under reduced pressure, then diatomaceous earth (1.0 g) was added thereto, stirred, and filtered to remove the enzyme protein.

Then first purification step, i.e. molecular distillation treatment, second purification step, i.e. treatment with the adsorbent, and third purification process, i.e. steam distillation treatment were carried out in the same manner as in EXAMPLE 5 and finally sterol fatty acid esters (59 g) were obtained.

The obtained sterol fatty acid esters had a purity of 95.2%, was almost tasteless, odorless and pale yellow in color. The analytic results are shown in Table 2.

EXAMPLE 7

Phytosterols (β-sitosterol content:42.5%) (50 g) and refined olive oil (100 g) were mixed and Vitamin E in an amount of 0.5% and bile salt of 2% based on the weight of the mixture were added thereto and dissolved at 60° C., then a suspension of lipolytic enzyme powder originated from a microorganism of the genus *Rhizopus* (60,000 units/g) (2.0 g) in water (50 g) was added thereto, and the synthetic reaction of a sterol fatty acid ester was carried out at 60° C. for 24 hours with stirring. Then the reaction mixture was heated to 100° C. and stirred at that temperature for 30 min. to inactivate the enzyme, subjected to washing with hot water, and dehydration at 80° C. under reduced pressure, then diatomaceous earth (1.0 g) was added thereto, stirred, and filtered to remove the enzyme protein.

Then first purification step, i.e. molecular distillation treatment, second purification step, i.e. treatment with the adsorbent, and third purification process, i.e. steam distillation treatment, were carried out in the same manner as in EXAMPLE 5 and finally sterol fatty acid esters (66 g) were obtained.

The obtained sterol fatty acid esters had a purity of 96.4%, was almost tasteless, odorless and pale yellow in color. The analytic results are shown in Table 2.

COMPARATIVE EXAMPLE 2

A synthetic reaction of a sterol fatty acid esters were carried out in the same manner as in EXAMPLE 5 and subjected to molecular distillation using a centrifugal molecular distillation apparatus at a vacuum pressure of 1.5 Pa and an evaporating surface temperature of 230° C., thereby giving sterol fatty acid esters (63 g).

Though the obtained sterol fatty acid ester had a purity of 93.2%, it had a strong bitterness and a characteristic pungent odor and was brown in color, thereby it had not suitable qualities for a food. The analytic results are shown in Table 2.

COMPARATIVE EXAMPLE 3

Phytosterols (β-sitosterol content:42.5%) (50 g) and refined soybean oil (100 g) were mixed and lipolytic enzyme powder originated from a microorganism of the genus *Pseudomonas* (50,000 units/g) (2.0 g) having an activity of decomposing sterol fatty acid esters were added and the synthetic reaction of sterol fatty acid esters were carried out at 40° C. for 24 hours with stirring. Then the reaction mixture was heated to 80° C. and stirred at that temperature for 30 min. to inactivate the enzyme, subjected to washing with hot water, and dehydration at 80° C. under reduced pressure, then diatomaceous earth (1.0 g) was added thereto, stirred, and filtered to remove the enzyme protein.

Then first purification step, i.e. molecular distillation treatment, second purification step, i.e. treatment with the adsorbent, and third purification process, i.e. steam distillation treatment, were carried out in the same manner as in EXAMPLE 5 and finally sterol fatty acid esters were obtained (86 g).

The obtained sterol fatty acid esters were almost tasteless, odorless and pale yellow in color, but the purity of the sterol fatty acid esters, 45.7%, were very low. The analytic results are shown in Table 2.

TABLE 2

| | | Ex. 5 | Ex. 6 | Ex. 7 | C. Ex. 2 | C. Ex. 3 |
|---|---|---|---|---|---|---|
| Sterol fatty acid esters content | TLC-FID % | 96.5 | 95.2 | 96.4 | 93.2 | 45.7 |
| Peroxide value (POV) | meq/kg | 1.8 | 1.5 | 1.9 | 3.6 | 1.5 |
| Acid value (AV) | mg-KOH/g | 0.1 | 0.2 | 0.2 | 0.9 | 0.3 |
| Color | Gardner Scale | 3 | 3 | 3 | 16 | 3 |
| Odor | Sensory Evaluation | almost odorless | Almost odorless | almost odorless | characteristic strong odor | almost odorless |
| Taste | Sensory Evaluation | tasteless | tasteless | tasteless | strong bitter taste | tasteless |

IDUSTRIAL APPLICABILITY

According to the present invention, there is provided an advantage that dietary sterol fatty acid esters having excellent physiological activities and superior qualities can be produced, by employing phytosterols and fatty acids as starting materials, performing the synthetic reaction of sterol fatty acid esters using a lipase as a catalyst under strictly controlled conditions, and by purifying the synthesized sterol fatty acid esters through several steps of purification process in order to provide qualities suitable for a food.

Furthermore, according to the present invention, there is provided an advantage that dietary sterol fatty acid esters having excellent superior qualities can be enzymatically produced by employing phytosterols and a fat and oil containing triacylglycerol as the main component, as the starting materials, performing the synthetic reaction of a sterol fatty acid ester using lypolytic enzyme as a catalyst under strictly controlled conditions, and purifying the synthesized sterol fatty acid esters through several steps of purification process in order to provide qualities suitable for a food.

What is claimed is :

1. A process for enzymatically producing physiological active dietary sterol fatty acid esters from phytosterols and fatty acids using a lipase as a catalyst, the process comprising the steps of:
   providing fatty acids obtained by an enzymatic process or continuous high pressure decomposition process as a fatty acid source,
   performing a synthetic reaction of sterol fatty acid esters using a lipase for predetermined time period under the conditions where temperature and water content are controlled,
   performing inactivation of the lipase, dehydration and removal of the lipase,
   performing a molecular distillation to remove unreacted sterols and fatty acids,
   treating a resulting product with an adsorbent to remove coloring components, and
   performing a steam distillation to remove odorous components, and thereby
   obtaining sterol fatty acid esters which are superior in sensory properties and safety and suitable for a food.

2. The process for producing dietary sterol fatty acid esters according to claim 1, wherein the synthetic reaction of sterol fatty acid esters by lipase is performed while the water content is controlled to be 50% or less based on the amount of the starting material sterols.

3. The process for producing dietary sterol fatty acid esters according to claim 1, wherein the lipase is a mesophilic lipase, and the synthetic reaction of sterol fatty acid esters are performed at 30 to 50° C. within 48 hours.

4. The process for producing dietary sterol fatty acid esters according to claim 1, wherein the lipase is a thermostable lipase, and the synthetic reaction of sterol fatty acid esters is performed at 50 to 80° C. within 24 hours, and a substance capable of inhibiting the inactivation of an enzyme is added when the synthetic reaction of sterol fatty acid esters are carried out by the lipase, and a substance having anti oxidant action is added when the synthetic reaction of sterol fatty acid esters are carried out by the lipase.

5. The process for producing dietary sterol fatty acid esters according to claim 1, wherein unreacted free sterols and fatty acids are removed by the molecular distillation performed using a molecular distillation apparatus at 13.3 Pa or lower and 150 to 250° C. and the molecular distillation treatment being repeated several times.

6. The process for producing dietary sterol fatty acid esters according to claim 1, wherein the treatment with an adsorbent is performed using, as the adsorbent, activated clay in an amount of 1 to 20% based on the weight of the materials to be treated, in the presence of an organic solvent.

7. The process for producing dietary sterol fatty acid esters according to claim 1, wherein the steam distillation to remove odorous components is carried out at 1330 Pa or lower and at 100 to 150° C. to prevent the generation of trans fatty acids.

8. The process for producing dietary sterol fatty acid esters according to claim 1, wherein the obtained sterol fatty acid esters have sterol fatty acid esters content of 90 wt % or more, the peroxide value of 15 or lower, the acid value of 3 or lower and a Gardner color scale of 6 or lower and is almost odorless as determined by a sensory test.

9. The process for producing dietary sterol fatty acid esters according to claim 1, wherein the lipase is added in a step wise manner.

10. A method for using dietary sterol fatty acid esters as recited in claim 1 for food in the form where the sterol fatty acid ester is previously mixed with a fat and oil primarily comprising triacylglycerol.

11. A process for producing dietary sterol fatty acid esters, the process comprising the steps of:
   providing phytosterols and fats and oils comprising triacylglycerols as starting materials,
   performing a synthetic reaction of sterol fatty acid esters by a lipolytic enzyme for a predetermined time period in a system wherein temperature and water content are controlled,
   as a first purification step, performing a molecular distillation to primarily remove unreacted sterols and fatty acids,
   as a second purification step, treating a resulting product with an adsorbent, to primarily remove coloring components,
   as a third purification step, performing a steam distillation to primarily remove odorous components, thereby obtaining a sterol fatty acid ester which is superior in sensory properties and safety as a food.

12. The process for producing dietary sterol fatty acid esters according to claim 11, wherein the phytosterols used as the starting material contain β-sitosterol in an amount of 20 to 80% by weight.

13. The process for producing dietary sterol fatty acid esters according to claim 11, wherein fats and oils primarily comprising triacylglycerol is one or an admixture of two or more kinds of oils selected from the group consisting of soybean oil, rapeseed oil, and olive oil.

14. The process for producing dietary sterol fatty acid esters according to claim 11, wherein an enzyme having an activity of degrading sterol fatty acid esters are employed as the lipolytic enzyme.

15. The process for producing dietary sterol fatty acid esters according to claim 11, wherein an enzyme having triacylglycerols decomposition activity is employed as the lipolytic enzyme.

16. The process for producing dietary sterol fatty acid esters according to claim 15, wherein the enzyme having triacylglycerol decomposition activity is cholesterol esterase or lipase.

17. The process for producing dietary sterol fatty acid esters according to claim 11, wherein the synthetic reaction of sterol fatty acid esters by lipolytic enzyme is performed for a predetermined time period in a system wherein temperature and water content are controlled; in which the reaction is performed at 30 to 60° C. within 48 hours while the water content is controlled to be 0.1 to 50% based on the weight of the starting materials.

18. The process for producing dietary sterol fatty acid esters according to claim 11, wherein the synthetic reaction of sterol fatty acid esters by lipolytic enzyme is performed for a predetermined time period in a system wherein temperature and water content are controlled; in which the reaction is performed in the presence of a substance capable of inhibiting the inactivation of an enzyme and a substance having anti oxidant action, by employing a thermostable lipolytic enzyme, at 50 to 90° C. within 48 hours while the water content is controlled to be 0.1 to 50% based on the weight of the starting materials.

19. The process for producing dietary sterol fatty acid esters according to claim 11, wherein the synthetic reaction of sterol fatty acid esters is performed using a lipolytic enzyme which is originated from a microorganism of the genus *Rhizopus* as the thermostable lipolytic enzyme.

20. The process for producing dietary sterol fatty acid esters according to claim 11, wherein the molecular distillation as the first purification step to remove primarily unreacted sterols and fatty acids is performed at 13.3 Pa or lower and at 100 to 250° C.

21. The process for producing dietary sterol fatty acid esters according to claim 11, wherein the treatment with an adsorbent as the second purification step to remove primarily coloring components is performed at 100° C. or lower using, as the adsorbent, activated clay in an amount of 0.1 to 50% based on the weight of the materials to be treated.

22. The process for producing dietary sterol fatty acid esters according to claim 11, wherein the steam distillation as the third purification step is performed to remove odorous components, and by performing it at 1330 Pa or lower and at 50 to 150° C., generation of trans fatty acids is prevented.

23. The process for producing dietary sterol fatty acid esters according to claim 11, wherein the end product sterol fatty acid esters has a sterol fatty acid esters content of 90 wt % or more, the peroxide value of 15 or lower, the acid value of 3 or lower and a Gardner color scale of 6 or lower and is almost odorless as determined by a sensory test.

24. The process for producing dietary sterol fatty acid esters according to claim 15, wherein the enzyme having triacylglycerol decomposition activity is cholesterol esterase or lipase.

25. The process for producing dietary sterol fatty acid esters according to claim 6, wherein the organic solvent is hexane.

* * * * *